United States Patent [19]

Rokach et al.

[11] Patent Number: 4,717,736
[45] Date of Patent: Jan. 5, 1988

[54] ANTAGONISTS OF SLOW REACTING SUBSTANCES OF ANAPHYLAXIS

[75] Inventors: Joshua Rokach, Chomedey, Laval, Quebec; Robert N. Young, Senneville, Quebec, both of Canada

[73] Assignee: Merck Frosst Canada, Inc., Kirkland, Quebec, Canada

[21] Appl. No.: 673,649

[22] Filed: Nov. 21, 1984

Related U.S. Application Data

[63] Continuation-in-part of Ser. No. 573,170, Jan. 23, 1984, abandoned.

[51] Int. Cl.[4] .................. A61K 31/215; A61K 31/325; A61K 31/195; A61K 31/40; C07C 103/84; C07D 207/08

[52] U.S. Cl. .................. 514/539; 514/423; 514/482; 514/486; 514/487; 514/522; 514/533; 514/535; 514/555; 514/556; 514/562; 514/563; 548/533; 558/412; 558/413; 558/415; 558/416; 558/394; 560/9; 560/12; 560/13; 560/18; 560/21; 560/27; 560/34; 560/39; 560/40; 562/426; 562/430; 562/432; 562/435; 562/439; 562/444; 562/445; 562/448

[58] Field of Search .............. 514/562, 563, 564, 566, 514/486, 487, 533, 539, 522, 400, 419, 423, 482, 535, 555, 556; 260/465 D, 501.1, 501.13, 501.17, 501.19, 501.21; 560/9, 12, 16, 39, 41, 37, 42, 13, 18, 21, 27, 34, 40; 562/426, 430, 444, 450, 432, 435, 439, 445, 448; 548/344, 496, 533; 558/412, 413, 415, 416, 394

[56] References Cited

U.S. PATENT DOCUMENTS

| | | | |
|---|---|---|---|
| 3,043,868 | 7/1962 | Krimmel | 560/41 X |
| 3,452,079 | 6/1969 | Shen et al. | 560/9 X |
| 3,649,679 | 3/1972 | Marshall | 424/309 X |
| 3,706,792 | 12/1972 | Shen et al. | 424/303 X |
| 4,250,192 | 2/1981 | Sallmann et al. | 560/41 X |
| 4,386,031 | 5/1983 | Hilboll et al. | 560/41 X |
| 4,440,941 | 4/1984 | Suh et al. | 560/41 X |
| 4,448,729 | 5/1984 | Klaubert et al. | 560/43 X |
| 4,582,857 | 4/1986 | Grill et al. | 562/444 X |

FOREIGN PATENT DOCUMENTS 2118184 10/1983 United Kingdom .

Primary Examiner—Donald B. Moyer
Assistant Examiner—Patricia M. Scott
Attorney, Agent, or Firm—Gabriel Lopez; Hesna J. Pfeiffer; Paul H. Ginsburg

[57] ABSTRACT

Compounds having the formula:

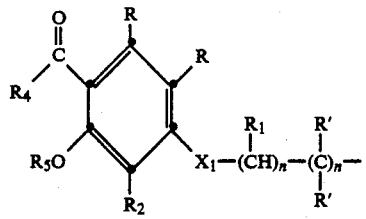

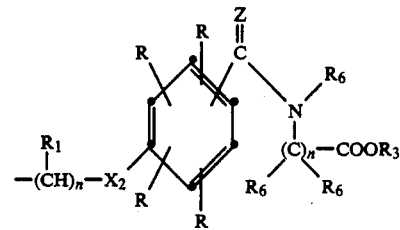

are antagonists of leukotrienes of $C_4$, $D_4$ and $E_4$, the slow reacting substance of anaphylaxis. These compounds are useful as anti-asthmatic, anti-allergic, anti-inflammatory agents and cytoprotective agents.

14 Claims, No Drawings

ANTAGONISTS OF SLOW REACTING SUBSTANCES OF ANAPHYLAXIS

This application is a continuation-in-part of U.S. Ser. No. 573,170, filed Jan. 23, 1984, now abandoned.

This invention is directed to compounds which act as antagonists of the slow reacting substances of anaphylaxis (SRS-A).

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that blocking the production or effects of 5-lipoxygenase products may suppress antigen-induced mast cell degranulation, an effect not observed with cortico steroids. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelsson, *Science*, 220 568 (1983).

Several classes of compounds exhibit ability to antagonize the action of leukotrienes in mammals, especially humans. See for example: Great Britain Patent Specification No. 2,058,785; and European Patent Application Nos. 56,172 and 61,800.

The present invention relates to compounds having activity as leukotriene and SRS-A antagonists, to methods for their preparation, to intermediates useful in their preparation and to methods and pharmaceutical formulations for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems, for example, actions such as result in angina. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of the present invention may be administered by insufflation, intravenously, rectally, topically, parenterally including subcutaneously and intramuscularly, or nasally.

The compounds of the present invention have the Formula I:

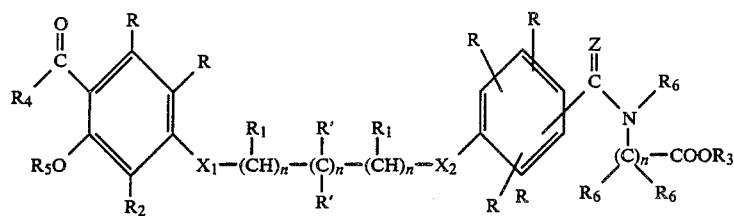

wherein each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen; amino; $N(R_3)_2$; phenyl; $COOR_3$; $CH_2OR_3$; formyl; CN; trifluoromethylthio; or nitro;

each R' is independently $R_3$; $OR_3$; or together R' and R' are doubly bonded O or $CH_2$;

each $R_1$ is independently H or alkyl of 1 to 4 carbons;

$R_2$ is alkyl of 1 to 6 carbon atoms which may be straight chain or branched; or alkenyl of 3 to 6 carbon atoms which may be straight chain or branched;

each $R_3$ is independently H or alkyl of 1 to 6 carbon atoms which may be straight chain or branched;

$R_4$ is H, alkyl of 1 to 6 carbon atoms which may be straight chain or branched; alkoxy of 1 to 6 carbon atoms which may be straight chain or branched;

$R_5$ is H; alkyl of 1 to 6 carbon atoms which may be straight chain or branched; $R_3CO-$ or $R_3OCH_2-$;

each $R_6$ is independently $R_3$ or is such that the structure $HNR_6-(CR_6R_6)_n-COOR_3$ is an amino acid or ester thereof;

$X_1$ and $X_2$ are independently oxygen, sulfur, sulfoxide, sulfone;

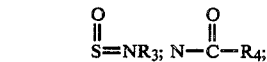

N—CN; or $NCONHR_3$;

Z is selected from O, S or $NR_3$; each n is independently an integer from 0 to 6;

and a pharmaceutically acceptable salt or acid addition salt thereof.

A preferred series of compounds have the Formula Ia:

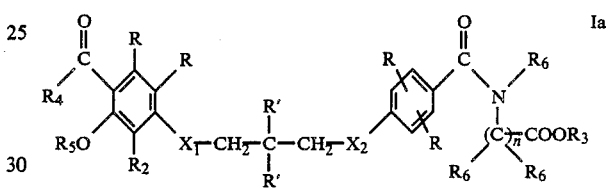

wherein: R, R', $R_2$, $R_3$, $R_4$, $R_5$ and $R_6$ are as defined for Formula I, and $X_1$ and $X_2$ are independently oxygen, sulfur, sulfoxide or sulfone.

As used herein, the term "amino acid, includes, but is not limited to the following amino acid structures; alanine, arginine, asparagine, aspartic acid, cysteine, glutamic acid, glycine, histidine, 5-hydroxylysine, 4-hydroxyproline, isoleucine, leucine, lysine, methionine, phenylalanine, proline, serine, threonine, tryptophan, valine, 3,4-dihydroxyphenylalanine, alpha-methylserine, alpha-methylphenylalanine, alpha-methylalanine, alpha-methylhistidine, alpha-methyl-3,4-dihydroxyphenylalanine, gammaaminobutyric acid, sarcosine, and the like.

As used herein, the term halogen includes fluorine, chlorine, bromine and iodine.

SCHEME I

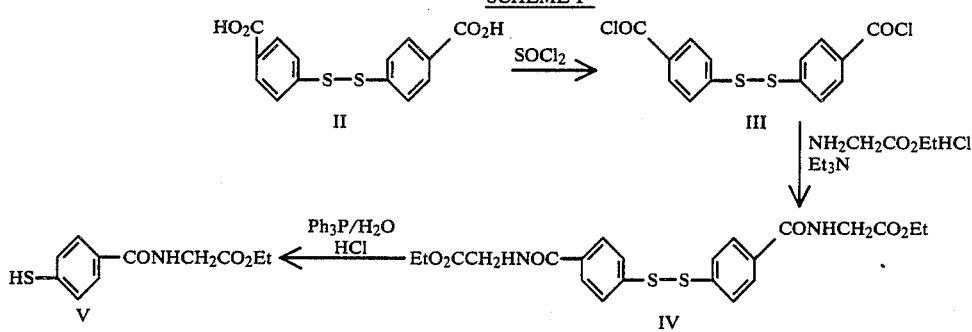

SCHEME I

-continued

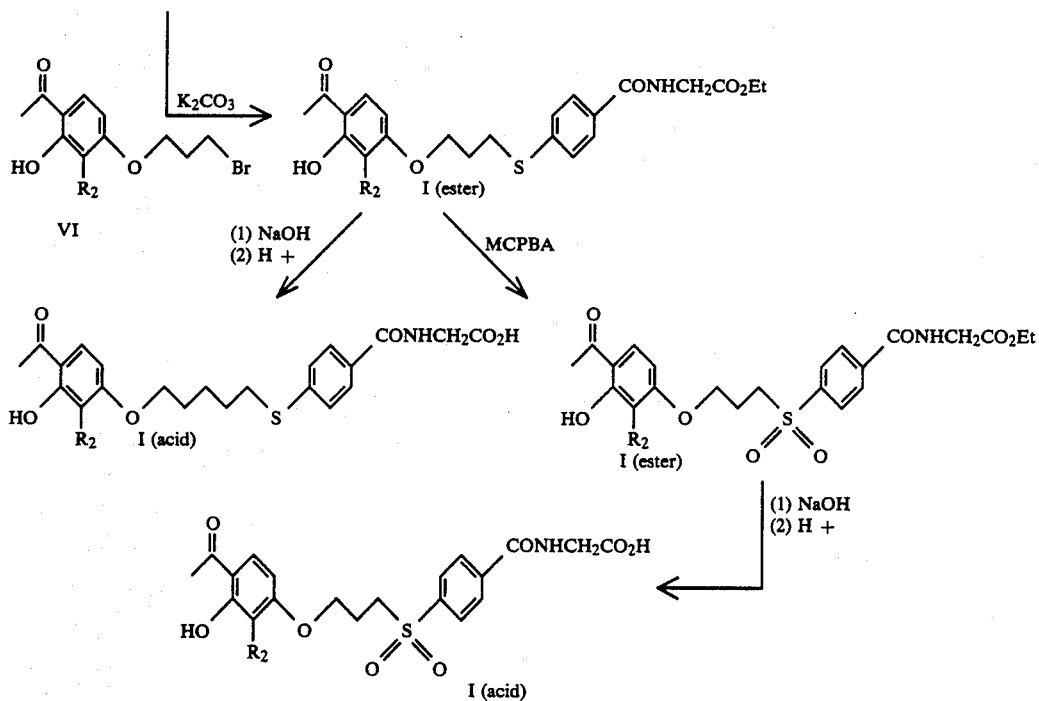

SCHEME II

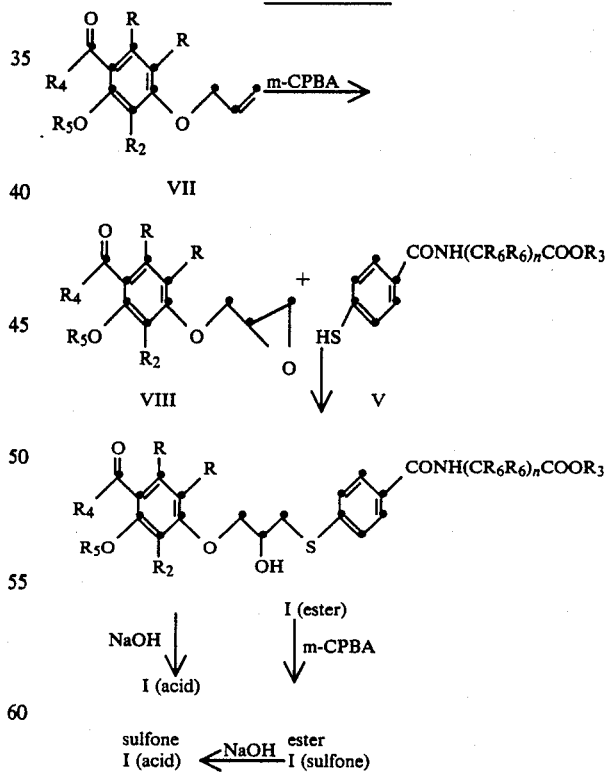

The compounds of the present invention may be prepared by several different routes. According to one method, illustrated in Scheme I, a compound of formula II, 4,4'-dithiobenzoic acid is converted to its acid chloride of formula III by treatment with thionyl chloride. Reaction of the acid chloride with an appropriate amino acid salt in the presence of a base such as triethylamine, affords the compound of formula IV. Treatment of the formula IV compound with triphenylphosphine and an acid, affords the mercaptan of formula V. Reaction of the bromoacetophenone derivative VI or its corresponding chloride or iodide in the presence of a base, such as potassium carbonate in a solvent such as methyl ethyl ketone gives rise to the ester of formula I. Other suitable bases could be an alkali metal carbonate such as $Li_2CO_3$, or $Na_2CO_3$. The reaction could also be carried out in other solvents such as THF, glyme, diglyme or DMF. The temperature range to carry out this transformation is 25°–160° C., the optimum being 60°–70° C.

The ester of formula I may then be reacted with an organic peracid, such as, for example, m-chloroperbenzoic acid to give the sulfoxide or sulfone of compound I. The oxidation is best carried out in an inert solvent, such as $CH_2Cl_2$ but other solvents such as chloroform or dichloroethane can also be used.

The ester of formula I may be hydrolyzed to the corresponding carboxylic acid by treatment with first, a base, such as sodium hydroxide, followed by acidification, with an acid such as hydrochloric acid.

The sulfone ester may likewise be converted to the corresponding sulfone carboxylic acid in a similar manner.

An alternate preparation of I as illustrated in Scheme II involves the reaction of VIII and V under the conditions already used successfully for reacting V and VI.

The intermediate olefin of structure VII is first epoxidized by reacting it with an organic peracid such as m-chlorobenzoic acid to yield an epoxide derivative of structure VIII. It is then easily reacted with a compound of formula V to yield I.

An embodiment of this invention is a process for preparing compounds of the formula I:

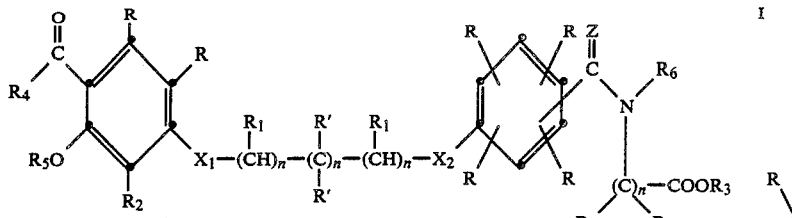

which comprises reacting a compound having the formula V:

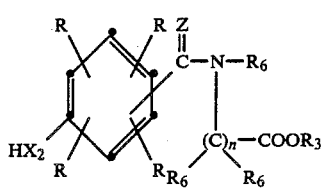

with a compound of formula VI:

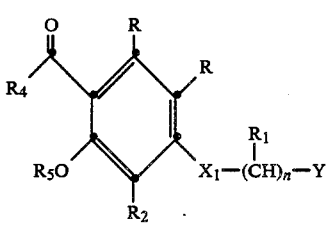

wherein Y is a halogen.

A further embodiment of this invention is a process for preparing compounds of the formula I:

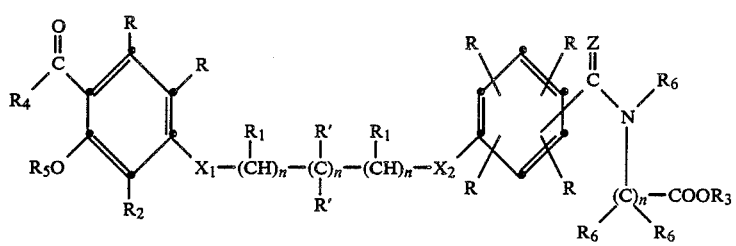

which comprises reacting a compound having the formula VIII:

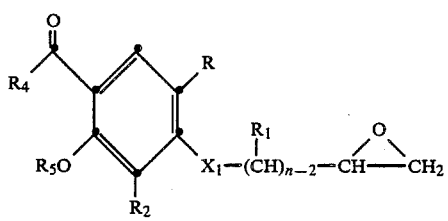

with a compound of formula V:

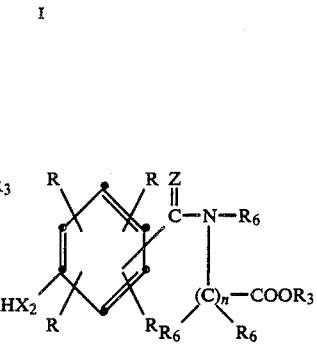

In those instances when asymmetric carbon atoms are present, more than one stereoisomer is possible, and all possible isomeric forms are deemed to be included within the planar structural representations shown. Optically active (R) and (S) isomers may be resolved using conventional techniques known to the skilled artisan, and all such isomers are considered to be within the scope of the present invention.

As indicated above, the compounds of Formula I are active as antagonists of SRS-A and the leukotrienes $B_4$, $C_4$, $D_4$ and $E_4$. This activity can be detected and evaluated by methods known in the art. See for example, Kadin, U.S. Pat. No. 4,296,129.

The ability of the compounds of Formula I to antagonize the effects of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. It will be understood that in this paragraph and in the discussion of methods of treatment which follows, references to the compounds of Formula I are meant to include the pharmaceutically acceptable salts or acid addition salts.

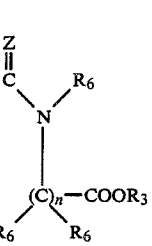

The cytoprotective activity of a compound may be observed in both animals and man by noting the increased resistance of the gastrointestinal mucosa to the noxious effects of strong irritants, for example, the ulcerogenic effects of aspirin or indomethacin. The addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of formula I will, of course, vary with the nature of the severity of the condition to be treated and with the particular compound of formula I and its route of administration. It will also vary according to the age, weight and response of the individual patient. In general, the daily dose range for anti-asthmatic, anti-allergic or anti-inflammatory use and generally, uses other than cytoprotective lies within the range of from about 0.2 mg to about 100 mg per kg body weight of a mammal, preferably 1 mg to about 100 mg per kg, and most preferably 5 to 40 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably, it is administered prior to or simultaneously with the NSAID (for example in a combination dosage form).

The effective daily dosage level for compounds of Formulae I inducing cytoprotection in mammals, especially humans, will generally range from about 0.02 mg/kg to about 100 mg/kg, preferably from about 0.2 mg/kg to about 20 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.2 mg to about 20 mg (preferably from about 1 mg to about 10 mg) of a compound of formula I per kg of body weight per day and for cytoprotective use from about 0.002 mg to about 40 mg (preferably from about 0.2 mg to about 20 mg and more preferably from about 1 mg to about 10 mg) of a compound of Formula I per kg of body weight per day. In the case where an oral composition is employed, a suitable dosage range for anti-asthmatic, anti-inflammatory or anti-allergic use is, e.g. from about 1 mg to about 100 mg of a compound of formula I per kg of body weight per day, preferably from about 5 mg to about 40 mg per kg and for cytoprotective use from about 0.2 mg to about 40 mg (preferably from about 0.2 mg to about 20 mg and more preferably from about 0.2 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques.

The carrier may take a wide variety of forms depending on the form of preparation desired for administration, e.g., oral or intravenous. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the leukotriene antagonists of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of Formula I:

| Injectable Suspension | mg/ml |
| --- | --- |
| Compound of Formula I | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of | 1 ml |

| Tablet | mg/tablet |
| --- | --- |
| Compound of Formula I | 25.0 |
| Microcrystalline Cellulose | 415.0 |
| Providone | 14.0 |
| Pregelatinized Starch | 43.5 |
| Magnesium Stearate | 2-2.5 |
| | 500 |

| Capsule | mg/capsule |
| --- | --- |
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, aluminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

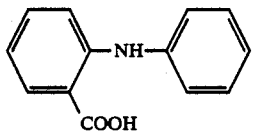

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/nonsteroidal anti-inflammatory drugs which contain the basic structure:

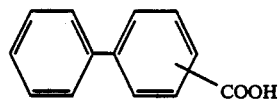

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

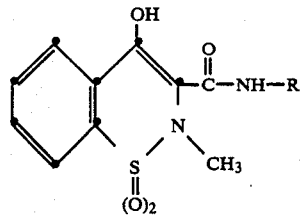

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TVX2706, U60257, UR2301, and WY41770.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent application Ser. No. 539,342, filed Oct. 5, 1983, now abandoned Ser. No. 459,924, filed Jan. 21, 1983, now abandoned, Ser. No. 539,215, filed Oct. 5, 1983, now abandoned, and Ser. No. 547,161, filed Oct. 31, 1983, now abandoned, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983, both of which are now abandoned, which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an H₁ or H₂-receptor antagonist, such as for instance cimetidine, ranitidine, terfenadine, famotidine, aminothiadiazoles disclosed in EP 40,696 and like compounds, such as those disclosed in U.S. Pat. Nos. 4,283,408; 4,362,736; and 4,394,508.

The pharmaceutical compositions may also contain a K+/H+ ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto. All temeratures are expressed in degrees Celsius.

EXAMPLE 1

4-(3-(4-Acetyl-3-hydroxy-2-propylphenoxy)propylthio)-N-(2-oxo-2-ethoxyethyl)benzamide

Step A: 4,4'-Dithiobisbenzoylchloride 4,4'-Dithiobisbenzoic acid (20 g) was refluxed in thionyl chloride (50 ml) for two hours. The reaction mixture was concentrated in vacuo and then coevaporated with toluene to afford the title compound which was used as such in the following step.

Step B: 4,4'-Dithiobis[N-(2-oxo-2-ethoxyethyl)]benzamide

The compound of Step A (6.523 mmoles) was combined with glycine ethyl ester hydrochloride (1.82 g, 2 eqts) and triethylamine (6 ml, 6 eqts) in dry toluene (100 ml). The reaction mixture was heated at reflux under nitrogen for sixteen hours. The mixture was concentrated in vacuo and the residue purified by chromatography on silica gel to afford the title compound.

NMR (90 MHz) (CDCl$_3$): 1.2 (t, 3H), 4.2 (m, 4H), 6.9 (broad t, 1H), 7.6 (m, 4H).

Step C: 4-(3-(4-Acetyl-3-hydroxy-2-propylphenoxy)propylthio)-N-(2-oxo-2-ethoxyethyl)benzamide The compound of Step B (1.8 g, 3.78 mmoles) was taken up in 1,2-dimethoxyethane (80 ml) to which was added triphenylphosphine (1.09 g, 1.1 eqts) and water (8 ml) containing two drops of concentrated HCl. The reaction mixture was stirred at room temperature for 16 hours, concentrated in vacuo and the residue taken up in chloroform, dried and concentrated in vacuo. The residue was taken up in methyl ethyl ketone (100 ml) to which was added 2-hydroxy-3-propyl-4-(3-bromopropoxy)acetophenone (2.38 g, 2 eqts) and potassium carbonate (2.5 g, 4 eqts). This mixture was refluxed under nitrogen for 16 hours. The mixture was filtered and the filtrate was concentrated in vacuo. The residue was purified by HPLC on silica gel to afford the title compound which was recrystallized from ether, m.p. 115°–116°.

Analysis, calculated: C, 63.41; H, 6.60; S, 6.77. Found: C, 63,61; H, 6.68; S, 6.47.

EXAMPLE 2

4-(3-(4-Acetyl-3-hydroxy-2-propylphenoxy)propylthio)-N-(carboxymethyl)benzamide

The compound of Example 1 (500 mg, 1.06 mmoles) was taken up in a mixture of THF (10 ml), 1N NaOH (2.2 ml) and water (7.8 ml). The reaction mixture was stirred at room temperature for three hours, then concentrated in vacuo. The residue was taken up in water, filtered, acidified with dilute HCl and extracted with chloroform. The combined chloroform extracts were dried and concentrated in vacuo to afford the title compound which was recrystallized from ethyl acetate/hexane, m.p. 133°–135° (dec.).

Analysis, calculated: C, 62.00; H, 6.11; S, 7.20. Found: C, 62.11; H, 6.34; S, 7.10.

EXAMPLE 3

4-(3-(4-Acetyl-3-hydroxy-2-propylphenoxy)propylsulfonyl)-N-(2-oxo-2-ethoxyethyl)benzamide The compound of Example 1 (400 mg, 0.845 mmoles) was taken up in methylene chloride (30 ml) to which was added m-chloroperbenzoic acid (343 mg, 2 eqts). The reaction mixture was stirred at room temperature under nitrogen for one hour. An additional 20 mg of m-CPBA was added and stirring was continued for one hour. Calcium hydroxide (400 mg) was added to the reaction mixture and stirring was continued for ten minutes. The reaction mixture was filtered and the filtrate was concentrated in vacuo. The residue was triturated with ether to afford the title compound, m.p. 138°–140°.

EXAMPLE 4

4-(3-(4-Acetyl-3-hydroxy-2-propylphenoxy)propylsulfonyl)-N-(carboxymethyl)benzamide The compound of Example 3 (430 mg, 0.851 mmoles) was taken up in a mixture of THF (10 ml), 1N NaOH (1.8 ml) and water (8.2 ml). The reaction mixture was stirred at room temperature under nitrogen for two hours. The THF was then removed in vacuo and the residue was diluted with water and filtered. The aqueous solution was acidified with dilute HCl and extracted with chloroform. The combined chloroform extracts were dried and concentrated in vacuo to afford the title compound which was recrystallized from ethyl acetate/hexane, m.p. 171°–173°.

Analysis, calculated: C, 57.85; H, 5.07; S, 6.71. Found: C, 57.92; H, 5.73; S, 6.74.

Using the above methodology the following Formula I compounds are also prepared:

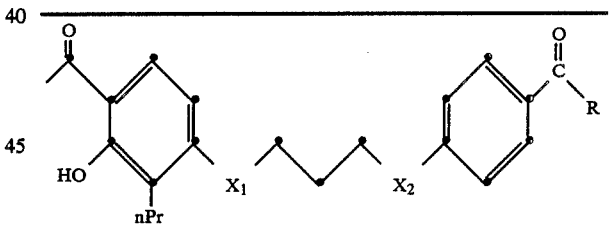

| Example | X$_1$ | X$_2$ | R | Amino Acid |
|---|---|---|---|---|
| 5 | O | S | —NHCH(CH$_3$)CO$_2$H | alanine |
| 6 | O | SO | —NHCH(CH$_3$)CO$_2$H | alanine |
| 7 | O | S | —NHCH[CH(CH$_3$)$_2$]CO$_2$H | valine |
| 8 | O | O | —N⟩CO$_2$H (proline ring) | proline |
| 9 | O | O | —NHCH(CH$_2$Ph)CO$_2$H | phenylalanine |
| 10 | O | S | —NHCH(CH$_2$CH$_2$SCH$_3$)CO$_2$H | methionine |
| 11 | O | S | —NH(CH$_2$)$_3$CO$_2$H | γ-aminobutyric acid |
| 12 | O | SO$_2$ | —NH(CH$_2$)$_3$CO$_2$H | γ-aminobutyric acid |
| 13 | O | S | —NHC(CH$_3$)(Ph)CO$_2$H | α-methyl- |

-continued

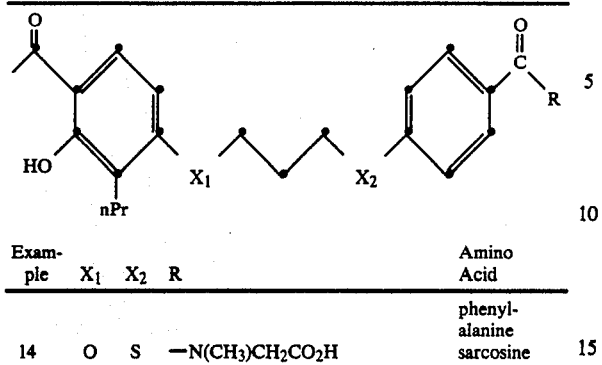

| Example | $X_1$ | $X_2$ | R | Amino Acid |
|---|---|---|---|---|
| 14 | O | S | $-N(CH_3)CH_2CO_2H$ | phenylalanine sarcosine |

In the compounds of Examples 5–14, nPr represents n-propyl and pH represents phenyl.

Claims to the invention follow.

What is claimed is:

1. A compound having the formula:

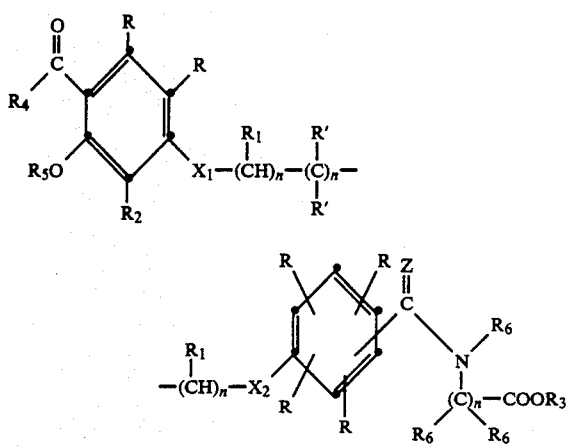

wherein: each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen; amino; $N(R_3)_2$; $COOR_3$; $CH_2OR_3$; formyl; CN; trifluoromethylthio; or nitro;

each R' is independently $R_3$; $OR_3$; or together R' and R' are doubly bonded O or $CH_2$;

each $R_1$ is independently H or alkyl of 1 to 4 carbons;

$R_2$ is alkyl of 1 to 6 carbon atoms which may be straight chain or branched; or alkenyl of 3 to 6 carbon atoms which may be straight chain or branched;

each $R_3$ is H or alkyl of 1 to 6 carbon atoms which may be straight chain or branched;

$R_4$ is H, alkyl of 1 to 6 carbon atoms which may be straight chain or branched; alkoxy of 1 to 6 carbon atoms which may be straight chain or branched;

$R_5$ is H; alkyl of 1 to 6 carbon atoms which may be straight chain or branched; $R_3CO-$ or $R_3OCH_2-$;

each $R_6$ is independently $R_3$ or is such that the structure $HNR_6-(CR_6R_6)_n-COOR_3$ is an amino acid or ester thereof;

$X_1$ and $X_2$ are independently oxygen, sulfur, sulfoxide, sulfone;

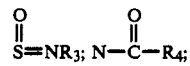

N—CN; or $NCONHR_3$;

Z is O;

each n is independently an integer from 0 to 6; and a pharmaceutically acceptable salt or acid addition salt thereof.

2. The compound of claim 1 wherein Z is oxygen, and each X is selected from oxygen, sulfur, sulfoxide or sulfone.

3. The compound of claim 1 wherein Z is oxygen and n is from 0 to 4.

4. The compound of claim 1 wherein Z is oxygen, each n is from 1 to 4, and each X is selected from oxygen, sulfur, sulfoxide or sulfone.

5. A compound according to claim 1 having the Formula Ia:

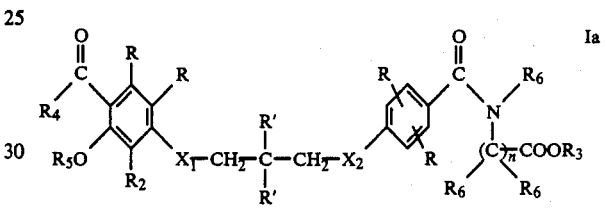

wherein: R, R', $R_2$, $R_3$, $R_4$, $R_5$ and $R_6$ are as defined for Formula I, and $X_1$ and $X_2$ are independently oxygen, sulfur, sulfoxide or sulfone.

6. The compound 4-(3-(4-Acetyl-3-hydroxy-2-propylphenoxy)propylthio)-N-(carbethoxymethyl)benzamide.

7. The compound 4-(3-(4-Acetyl-3-hydroxy-2-propylphenoxy)propylthio)-N-(carboxymethyl)benzamide.

8. The compound 4-(3-(4-Acetyl-3-hydroxy-2-propylphenoxy)propylsulfonyl)-N-(carbethoxymethyl)benzamide.

9. The compound 4-(3-(4-Acetyl-3-hydroxy-2-propylsulfonyl)-N-(carboxymethyl)benzamide.

10. The compound having the formula:

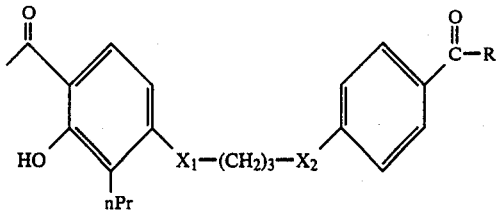

wherein the substituents are:

| $X_1$ | $X_2$ | R |
|---|---|---|
| O | S | $-NHCH(CH_3)CO_2H$ |
| O | SO | $-NHCH(CH_3)CO_2H$ |
| O | S | $-NHCH[CH(CH_3)_2]CO_2H$ |

| $X_1$ | $X_2$ | R |
|---|---|---|
| O | O | 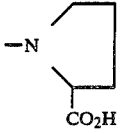 |
| O | O | —NHCH(CH$_2$Ph)CO$_2$H |
| O | S | —NHCH(CH$_2$CH$_2$SCH$_3$)CO$_2$H |
| O | S | —NH(CH$_2$)$_3$CO$_2$H |
| O | SO$_2$ | —NH(CH$_2$)$_3$CO$_2$H |
| O | S | —NHC(CH$_3$)(Ph)CO$_2$H |
| O | S | —N(CH$_3$)CH$_2$CO$_2$H | nPr represents n-propyl and Ph represents phenyl.

11. A pharmaceutical composition useful in antagonizing leukotriene action in mammals comprising an amount of a compound of claim 1 effective as a leukotriene antagonist and a pharmaceutically acceptable carrier.

12. A method of antagonizing leukotriene action in a mammal which comprises administering an amount of a compound of claim 1 effective as a leukotriene antagonist.

13. A method of claim 12 wherein the mammal is a human.

14. A method of inducing gastric cytoprotection in mammals comprising administering to a mammal in need of such treatment a gastric cytoprotective amount of a compound of claim 1.

* * * * *